United States Patent [19]

Hall

[11] Patent Number: 4,807,469

[45] Date of Patent: Feb. 28, 1989

[54] MONITORING DRILLING MUD CIRCULATION

[75] Inventor: Christopher Hall, Stapleford, England

[73] Assignee: Schlumberger Technology Corporation, Houston, Tex.

[21] Appl. No.: 164,614

[22] Filed: Mar. 7, 1988

[30] Foreign Application Priority Data

Mar. 9, 1987 [GB] United Kingdom ............... 8705503

[51] Int. Cl.$^4$ ............................................. E21B 49/08
[52] U.S. Cl. ...................................... 73/155; 166/250; 175/42; 436/27
[58] Field of Search ...................... 73/155; 436/27, 28, 436/29; 166/250; 175/42

[56] References Cited

U.S. PATENT DOCUMENTS

| | | | |
|---|---|---|---|
| 4,352,674 | 10/1982 | Féry | 166/250 |
| 4,397,181 | 8/1983 | Caldwell | 73/155 |
| 4,447,340 | 5/1984 | Féry | 175/42 |
| 4,507,552 | 3/1985 | Roesner et al. | 73/155 |
| 4,722,394 | 2/1988 | Wellington et al. | 73/155 |

Primary Examiner—Michael J. Tokar
Assistant Examiner—Kevin D. O'Shea
Attorney, Agent, or Firm—Stephen L. Borst

[57] ABSTRACT

For monitoring drilling mud circulation there is incorporated in the supply mud a known amount or concentration of at least one tracer ion which is substantially non-interactive with the other mud components and with the strata drilled, and the return or circulatory mud is analyzed at the rig site (preferably by ion chromatography) for the non-interactive ion(s) to give an indication or annular dispersion. Preferably at least two tracer ions (e.g. a tracer compound providing a non-interactive cation and non-interactive anion) are used, these being analyzed independently in the return or circulatory mud to give separate checks on annular dispersion. Preferably the tracer is injected discontinuously into the supply mud, in spaced discrete relatively concentrated doses, and the residence time distribution of the tracer is plotted for each dose.

13 Claims, 8 Drawing Sheets

MONITORING DRILLING MUD CIRCULATION

The present invention relates to monitoring with tracers the circulation of drilling mud in a well during drilling.

Tracers are used in the well drilling industry for several purposes. One of them is to determine the "lag time" of the drilling mud to travel from the surface down the hole, through the drill bit and up to the surface again. Pellets of calcium carbide enclosed in a water-proof container are injected at the surface of the well being drilled and are carried down the well by the mud stream. When passing through the drill bit, the container is smashed releasing the calcium carbide reacts with water of the mud to form a gas, acetylene, which is detected at the surface with a gas analyser. The lag time can therefore be determined from the time difference between the injection of the calcium carbide in the well and the detection of gas at the surface in the return mud.

Tracers are also added to a drilling fluid in order to distinguish filtrate water from connate water. A tracer solution is slowly added to the drilling fluid over several circulations to ensure an even concentration throughout the drilling mud. Samples of the mud returning to the surface are frequently taken and analysed to monitor tracer concentration levels. From the concentration of the tracer in the samples, the extent of contamination of formation fluid by filtrate water can be assessed.

Another use of tracers relates to the injection of tracers in one well, followed by their detection in an adjacent well so as to make well-to-well correlations, enabling the characterization of the underground formation traversed by the two wells.

Various chemicals have been used as tracers in boreholes. For example, GB patent application No. 2,066,951 describes a method of tracing a well drilling mud by determining the concentration of acetate tracer ion in the strata penetrated (by the analysis of cores). The use as tracers of dichromate, chromate, nitrate, ammonium, cobalt, nickel, manganese, vanadium and lithlium is also mentioned.

Tracers are also used in chemical reactors for which the residence time theory (used in the present invention) has been developed and applied, in order to predict the period of time during which a particle passing through a reactor stays in contact with a chemical contained in the reactor. Guidance in obtaining the residence time density function from discrete data sets has been given in the context of chemical reactors, for example in chapter 1 of the book "Mixing in Continuous Flow Systems" written by Nauman and Buffham and published by John Wiley and Sons, Inc. in 1983, or in the book "Models for Flow Systems and Chemical Reactors" written by Wen and Fan and published by Marcel Dekker, Inc. 1975. However, such a theory has never been applied to the liquids circulating in a borehole.

The lag time such as determined in the prior art is not accurate enough for certain applications, such as the interpretation of chemical logs, and, in addition, the dispersion of the tracers in the mud circulating in the annulus has not been taken into account.

Analyses of the changing composition of return or circulating mud as drilling proceeds are distorted by the annular hydrodynamic dispersion of the mud. For accurate monitoring of the circulating mud composition, it is important to quantify this distortion (which may itself vary as drilling proceeds). As an example, our co-pending GB patent application No. 87 05502 relates to a method of monitoring continuously the downhole chemical interactions between the drilling mud and the formation being drilled by analysing mud samples at the surface. It is therefore important to determine to that extent the hydrodyramic dispersion in the mud circulation system distorts the time-variation of the chemical composition variables measured at the surface, so as to produce chemical logs free of distortion effect.

The invention proposes a method for the monitoring of drilling mud circulation in a wellbore, by injecting in a discrete way a known amount or concentration of at least one tracer ion in the supply mud and by analysing on site the return mud for the tracer, said tracer ion being substantially non-interactive with the other mud components and with the strata drilled, the concentration of said tracer ion being measured, as a function of time, in the return mud and its residence time density function f(t) being determined from said measured concentration in order to assess the hydrodynamic dispersion of the circulating mud.

Preferably at least two tracer ions (e.g. a tracer compound providing a non-interactive cation and non-interactive anion) are used, these being analysed independently in the return or circulatory mud to give separate checks on annular dispersion. The tracer is injected discontinuously into the supply mud, in spaced discrete doses, and the residence time density function of the tracer is plotted for each dose. From this distribution, the mean residence time is determined. The transfer function of the mud circulation system is advantageously derived.

A preferred operation according to the invention involves injecting a quantity of tracer into the mud inlet at the surface; detecting quantitatively the time variation of the tracer concentration as it returns to the surface; processing the tracer return concentration data to obtain a residence time distribution for the circulation; using the time distribution to obtain information on the circulation: and optionally using the residence time distribution to produce chemical logs from which the distorting effects of annular dispersion have been removed.

Thus by deliberate addition of tracers it is possible to determine the characteristics of the dispersion of materials in the well. The mean residence time $t_r$ is a more accurate version. of the driller's lag time—the time taken for mud to make the round trip; the second and higher moments of the residence time density function f(t) characterise the circulation mixing by convection and diffusion. This is new information on the mud circulation which could provide information on cuttings transport, circulation characteristics prior to displacement for cementing, hole shape, etc. In addition, the residence time density function may be used in a deconvolution algorithm to generate surface chemical logs from which the distorting effects of annular dispersion have been removed. In addition, since the area under the tracer outflow concentration curve e.g., area under $C_{out}(t)$ in FIG. 8, is equal to the total amount of tracer material washed out from the well during circulation, a comparison of this quantity with the total amount injected into the well gives, by difference, a measure of fluid loss during circulation (provided the tracer is non-interactive with the mud components and the formation drilled). Furthermore, a comparison of the mean residence time of inert tracer material and of the mean residence time of active materials (such as potassium) which react with the borehole wall can indicate the extent of adsorption of the active materials. The higher moments of the residence time distribution give information on the amounts and locations of wall reactions in uncased sections of the wall.

The invention will now be described in more detail and by way of example with reference to the accompanying drawings, in which:

FIG. 1 indicates schematically a tracer monitoring system according to the invention;

Figure 1:
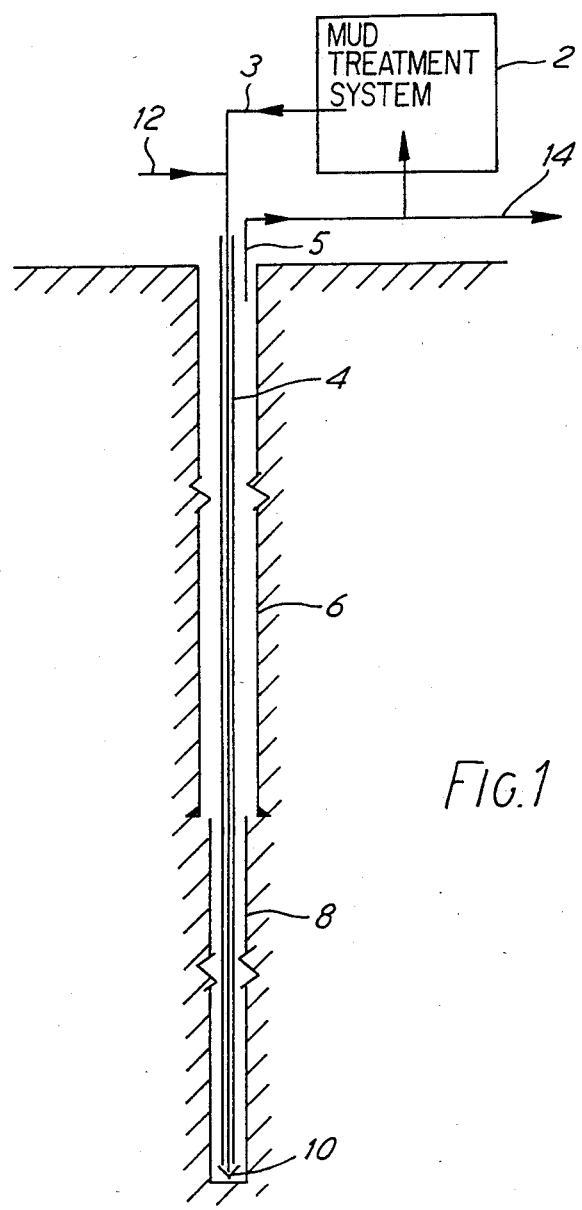

FIG. 1 illustrates schematically the drilling of a borehole by means of a drill string 4 having a drill bit 10 at its operating end, the upper end of the borehole being a cased hole 6 and the lower end an open hole 8. Mud 3 from a mud treatment system 2 is pumped down the drill string 4 to emerge at the bit end 10 and rises back up through the bore, return mud 5 being collected at 2 and treated for recirculation. In operation of the invention, a measured supply of monitoring tracer ion is injected into the mud supply at 12, and samples of return mud 5 are taken at 14 for analysis.

Preferably the tracer is injected into the downpipe 4 in the form of a compact plug of solid or dissolved material, in order to place in the circulating mud a sharp pulse of material. Because of the flow in the drill string is generally turbulent, little axial dispersion occurs on the journey to bottom hole and a compact pulse emerges through the bit. The tracer may be injected as a solid or as a concentrated solution.

Figure 2A:
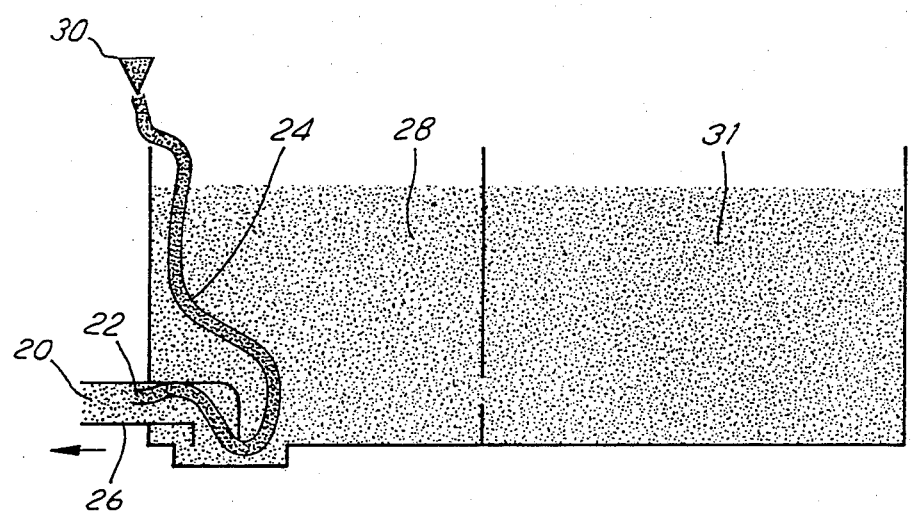
FIGS. 2A and 2B show schematically the arrangement used to inject the tracer and to collect samples of the returning mud.
Figure 2B:
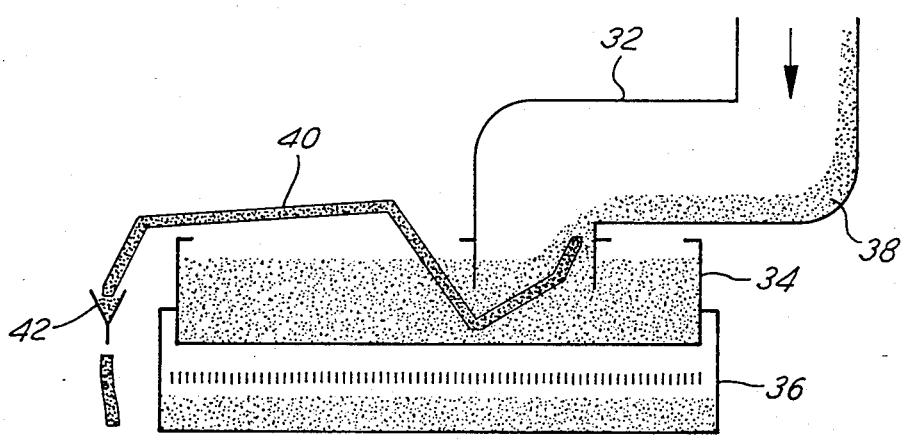

FIGS. 2A and 2B show schematically the arrangements for tracer injection and for sampling the return mud, respectively, which were used in experiments conducted in a well being drilled.

Tracer was injected into the mud stream 20 as a concentrated aqueous solution immediately before the high pressure mud pump (not shown). One end 22 of a flexible hose 24, preferably of a large diameter, was pushed about 1 meter into the oulet port 26 of the pill tank 28. The other end was connected to a funnel 30 mounted on the platform of the active mud tank. During experiments the pill tank 28 and the main active tank 31 were connected and the mud pump drew fluid from the pill tank. At the start of a tracer experiment tracer solution was gravity-fed into the mud stream, the mud pump itself acting as a mixing chamber. Tracer solution was completely flushed from the feed hose 24 with several liters of mud, maintaining roughly constant head throughout the addition.

The time for the concentrated tracer solution to enter the mud stream is known by direct observation and the initial tracer concentration can be calculated from the mixing ratio of mud and tracer. The total volumetric flow through the mud pump Q is accurately known from pump strokes and stroke volume; if a volume $V_t$ of tracer solution of concentration $c_t$ is injected into the mud stream in an interval of time dt, then the tracer concentration in the mud $c_m$ at the point of injection is given by:

$$c_m = c_t V_t / Qdt \tag{1}$$

The arrangement shown in FIG. 2A meets the main requirements for satisfactory tracer injection: the injection involves no interference with the normal circulation and it produces an initial concentration of tracer sufficiently small (typically 1 per cent by weight) that effects on mud density and rheology are almost certainly negligible. The tracer is added in accurately known amounts without losses or spillage. Instead of the simple arrangement shown on FIG. 2A, a metering pump for tracer injection could be connected directly to the line between the active tank and the mud pump. This pump, drawing fluid from a small reservoir of concentrated tracer solution, should be capable of injecting up to about 10 liters in a few seconds at a controlled but adjustable flow rate. The pump could also programed to inject a series of substantially rectangular tracer pulses.

Mud samples were collected (FIG. 2B) directly from the large feed pipe 32 which disgorges into the header box 34 of the shale shaker 36. This is the first point at which return mud appeared. The main concern was to sample the return mud 38 as far up-stream as possible, in order to eliminate from the first-pass measurements any effects due to residence in any of the elements of the solids control equipment. In order to sample the downflow of the feed pipe 32 before the mud entered the header box 34 of the shale shaker, a dog-leg tube 40 was placed within the large diameter feed pipe to divert a small mud stream to a position above the header box mud level. This sample stream was cascaded into a funnel 42 acting as a constant head device to create a steady flow which could be very conveniently sampled manually. The tubes and funnel of the sampling device had a very small capacity (relative to the flow rate) and mud passed through it very rapidly, in a few seconds at most. It proved possible with a little practice to collect a 60 ml mud sample in a screw-cap bottle every 15-20 seconds and to sustain this sampling rate for as long as one hour. However, the sampling could have been automated easily by feeding the continuous mud stream to a standard sample-bottle carousel for automatic collection and time-logging of the samples.

Choice of tracer is governed by the surface analytical system available. For use with an ion-chromatography system, a salt composed of metal ion and anion neither of which occur appreciably in muds or drilled formations is appropriate. Lithium broride, zinc bromide and others are suitable. Note that a salt provides two independently measurable species, cation and anion; these are independently convected and measurement of both two independent measurments of the residence time distribution. Provided that the tracer species do not adsorb on the bore hole wall, they are perfectly convected with the same velocity distribution as the mud itself. The residence time density function of the tracer is the same as that of the mud and of any other perfectly convected, inert species. A multi-component tracer (a tracer 'cocktail') inert to the mud elements but including substances both inert and active to the wellbore wall may be used to explore the chemical reactivity of the wellbore wall.

A surface analytical system is needed to detect the tracer as it returns to the surface. In addition to the equipment shown in FIGS. 2A and 2B, an ion chromatograph was used in the reported experiment to analyse the mud samples. Each sample was centrifuged and the solids-free supernatant was analysed for lithium. In the experiment, 2.5 kg of lithium bromide was used. The salt was dissolved in tap water to make about 3 liters of 9.4 mol/l solution. This was added to the mud stream by way of the feed-line 24 over a period of 16 seconds. The whole volume of tracer solution was added to the mud flow, mud being used to flush the feedline. The rate of addition was approximately constant over the 16 second injection period because the feed-line funnel acted as a crude constant-head device. During tracer addition, the pump rate was 22.25 l/s, so that by equation (1) the lithium bromide concentration in the input tracer pulse was 6.9 g/l (0.079 mol/l).

Figure 3:
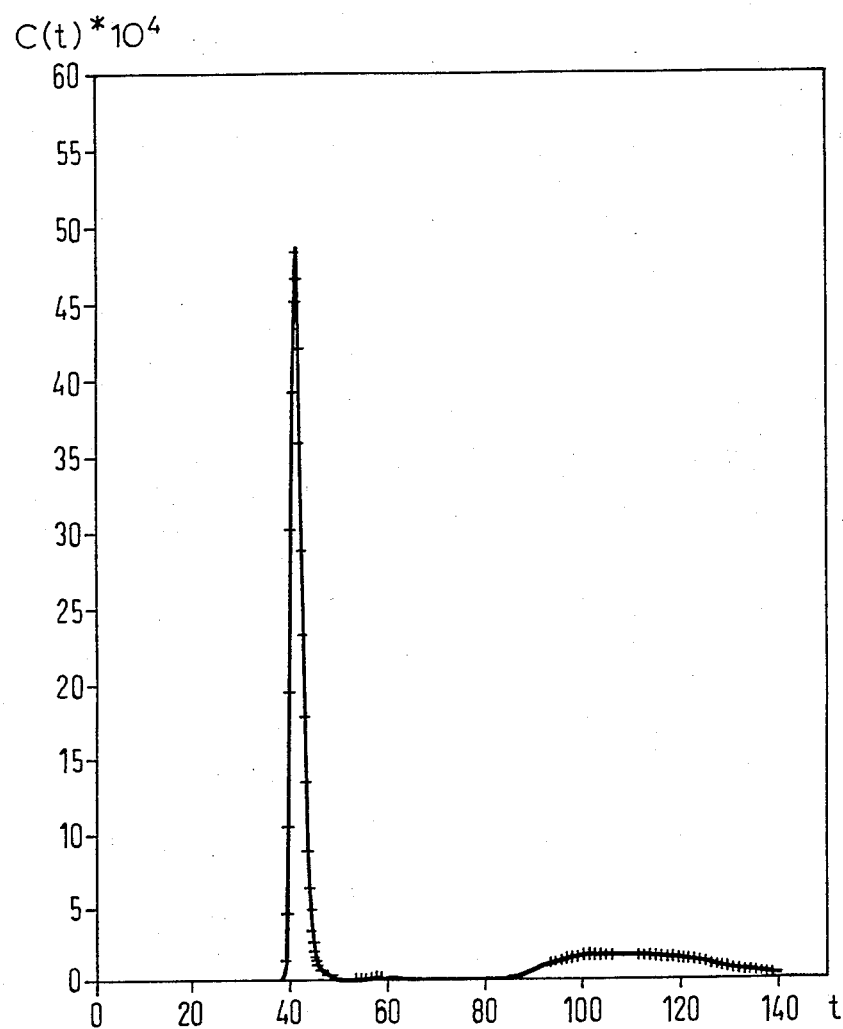
FIG. 3 represents the lithium concentration c(t) of the collected samples as a function of time t.

Because of mixing and dispersion effects in the annulus, the initially compact pulse of tracer was spread and washed out over a period of time, as in FIG. 3 which shows the lithium ion chemical log for the test, i.e., lithium ion concentration c(t) in $10^{-4}$ mol/l measured on the filtrate samples plotted against time t (in minutes), the initial time t=0 being the time of injection of the tracer.

Figure 4:
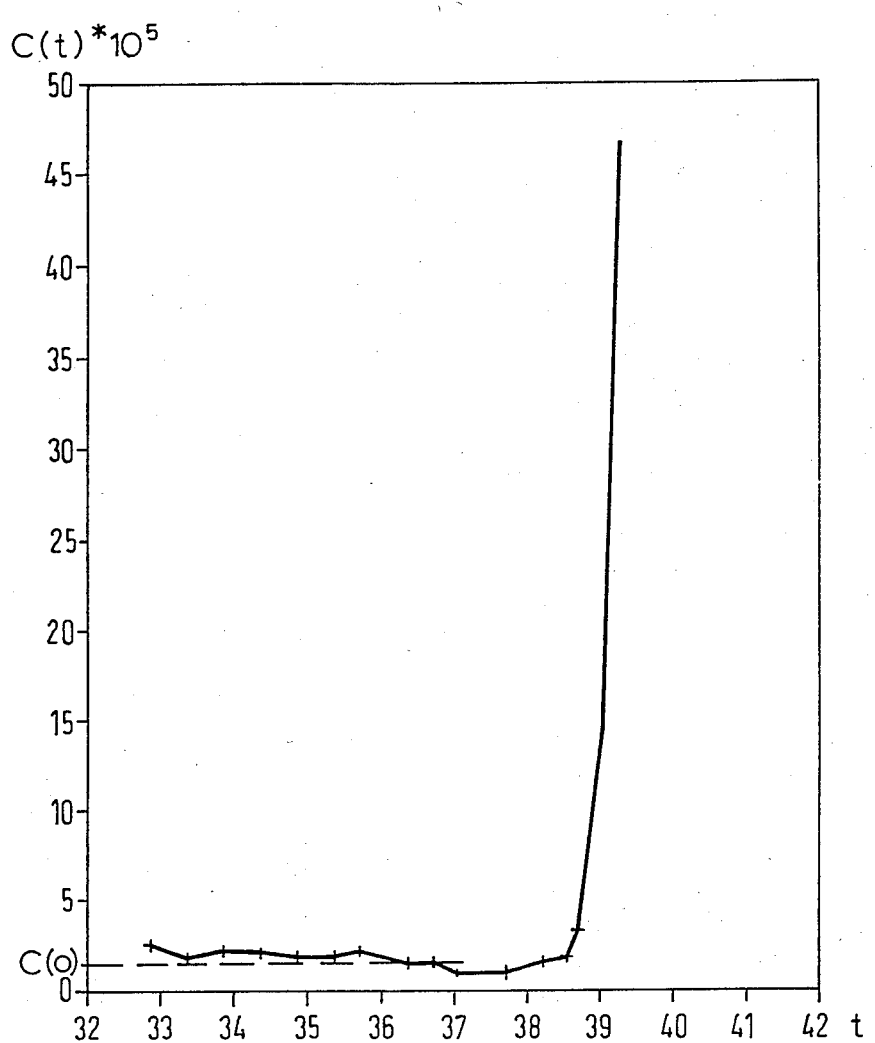
FIG. 4 shows the lithium background and the first appearance of detectable tracer above the background level.

FIG. 4 reproduces the first part of FIG. 3, with an expanded vertical scale, in order to determine the lithium background c(o) and the first appearance time $t_{fa}$ of detectable tracer above the background level, at t=39 minutes. The lithium background level, found to be c(o)=1.93 $10^{-5}$ mol/l, arose from the lithium bromide added to the mud in a preceding test which took place 19 hours previously.

Figure 5:
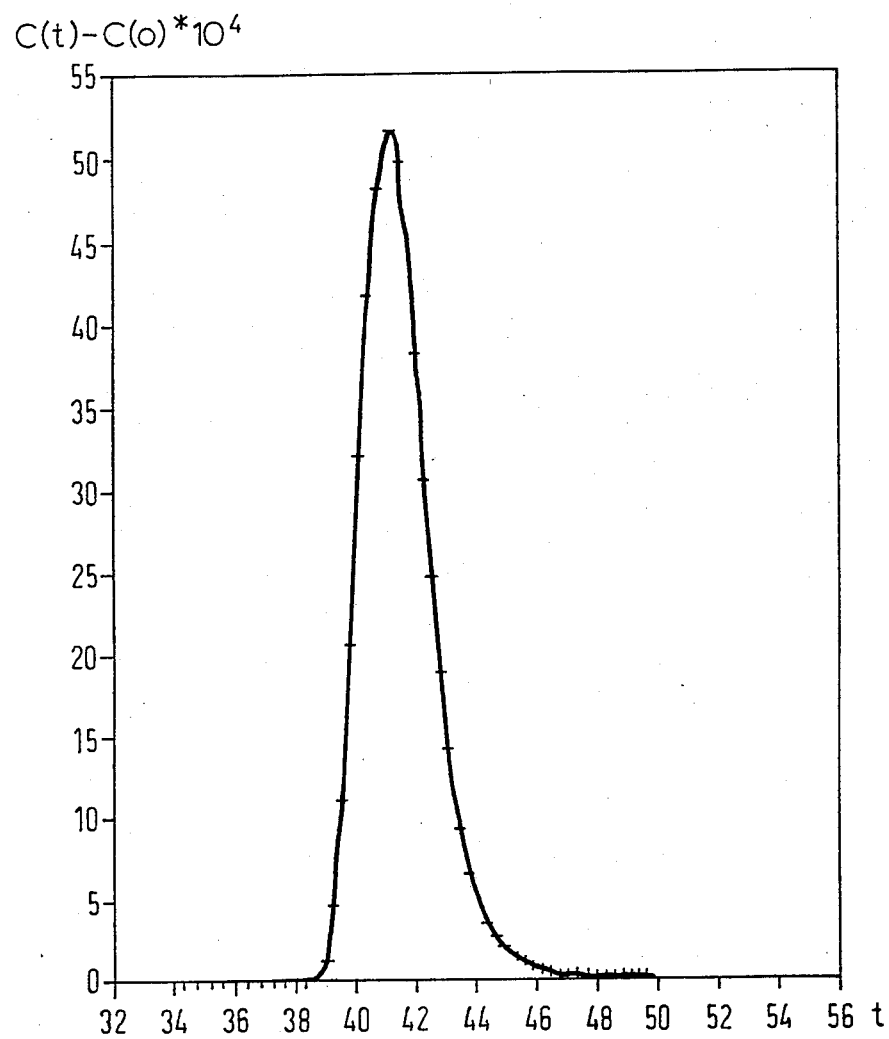
FIG. 5 represents the chemical log obtained for lithium, with baseline correction for background lithium plotted against time t.

FIG. 5 shows the concentration c(t)-c(o) of lithium with a baseline correction for the lithium (assumed constant throughout the test) plotted against time t. The area under the curve of FIG. 5 multiplied by the volumetric flowrate should be equal to the initial quantity of lithium injected in the well, provided there is no loss of fluid in the well and/or there is no retention of any kind, such as adsorption, of lithium by the wellbore wall. However, if the tracer is inert, any loss of tracer can be interpreted as a loss of fluid in the wellbore.

Then, c(t)-c(o) has been normalised by the integral of [c(t)-c(o)]dt, integrated as a function of time from t=0 to t=50 minutes, so as to define the residence time density function f(t) of the flow system:

$$f(t) = \frac{c(t) - c(o)}{\text{Integral } [c(t) - c(o)]dt}$$

Figure 6:
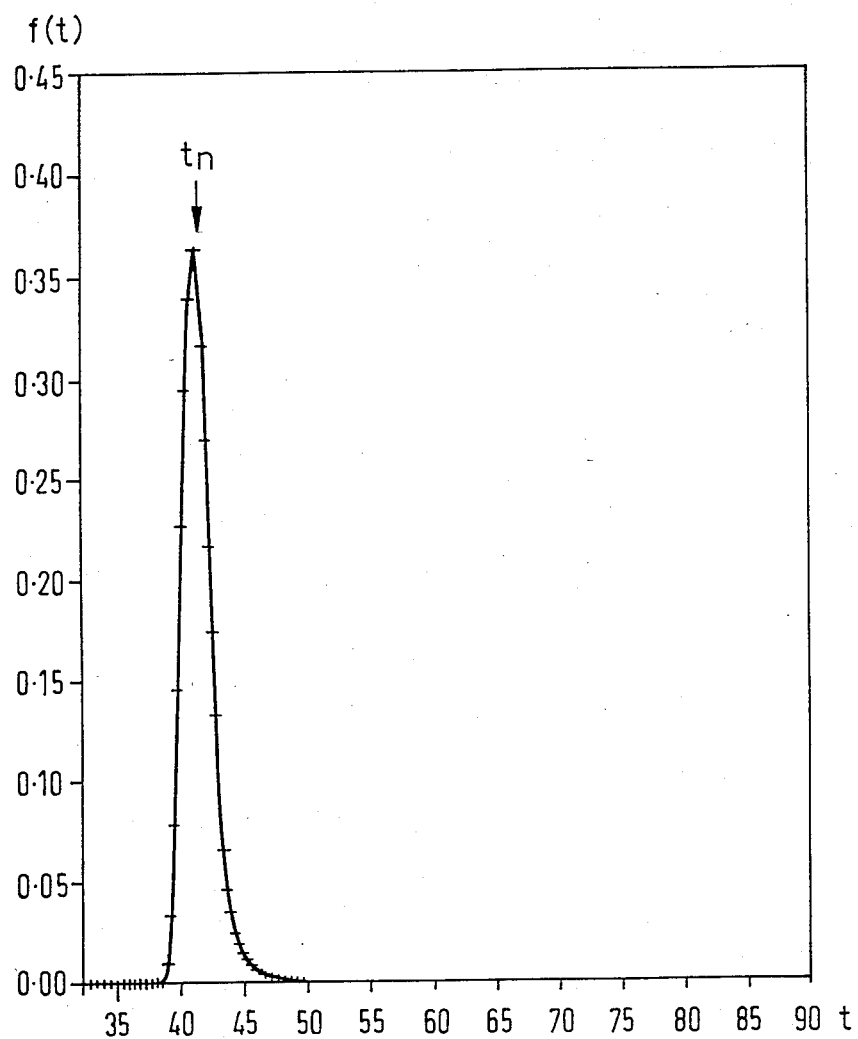
FIG. 6 represents the residence time density function f(t)

The time density function f(t) is shown on FIG. 6. The first moment of f(t) about t=0 is called the mean residence time $t_r$. Mathmatically expressed, the mean residence time $t_r$ is the integral of t.f(t).dt as a function of time from t=0 to t=infinity. $t_r$ has been found to be 41.54 min. $t_r$ is rigorously equal to V/Q where V is the system volume and Q the volume flow rate, so that V can be calculated (V=55.5 m$^3$). The time $t_r$ does not coincide with the maximum in f(t) because of the asymmetry of the curve.

The second moment of f about $t_r$ gives the variance of the residence time density, a measure of the spread of residence times and hence of the extent of hydrodynamic dispersion.

The concentration c(t)-c(o) of FIG. 5 has been interpreted as the impulse response of the subsystem comprising the pump, hole and return line, making no correction for the finite width of the tracer pulse, which was only 16 seconds in duration and was therefore practically a Dirac delta function.

Figure 7:
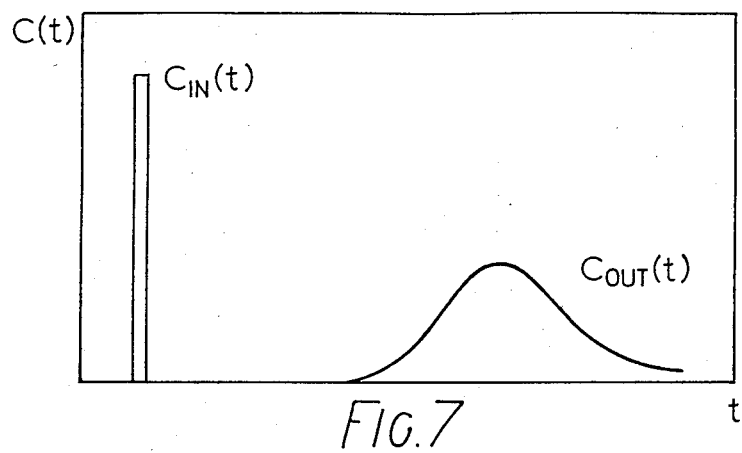
FIGS. 7 to 9 are various tracer concentration versus time graphs illustrating features of the invention.

The function f(t) of FIG. 6 obtained from the circulation of an initially compact pulse of tracer is the impulse response function of the system. Referring to FIG. 7 which illustrates the principle, the transfer function T of the mud circulating system may be determined as the normalised outlet concentration $C_{out}$ produced in response to an impulse input Cin represented by a Dirac delta function.

Figure 8:
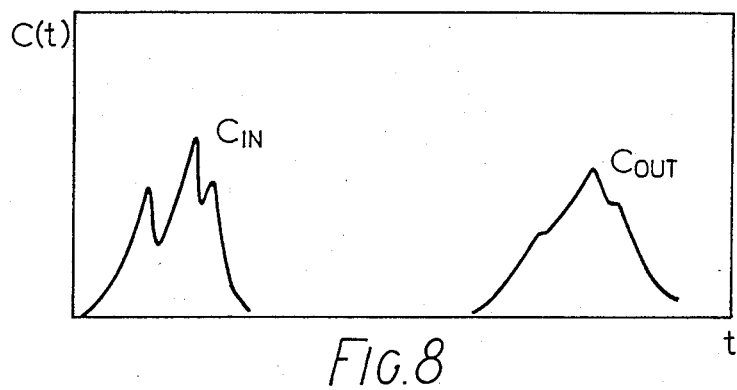

By convolving the transfer function with an arbitrary input $C_{in}(t)$, the outlet concentration $C_{out}(t)$ arising from input $C_{in}(t)$ may be computed (FIG. 8). Alternatively, by deconvolving the output $C_{out}$ with the transfer function, the input $C_{in}$ may be obtained from an output measurement $C_{out}$. An important application of this is in processing time series chemical logs to remove the effects of annular circulation. By deconvolving the output concentration data obtained by analysing the return mud with the transfer function, logs are obtained which are corrected for the hydrodynamic dispersion ocurring in the circulation mud and therefore which more accurately correspond to time-varying downhole processes, such as lithology changes at the bit and influxes.

Figure 9:
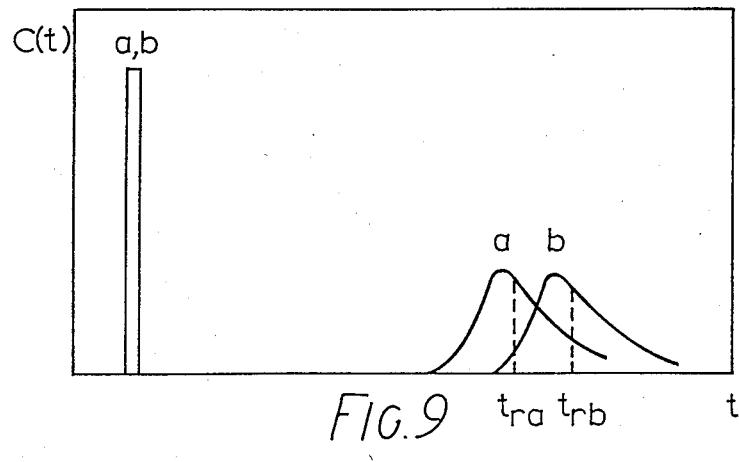

If any tracer (or an individual component of a tracer mixture) is reversibly adsorbed on the wellbore wall (for example, by ion exchange with an active shale) the residence time density function f(t) of this species will differ from that of an inert tracer. As shown in FIG. 9, a tracer [b] which is adsorbed on the bore hole wall remains in the system longer than an inert tracer [a]. The ratio of mean residence times depends on the adsorption behaviour of b. In particular, the mean residence time $t_{rb}$ for tracer [b] will be longer than that $t_{ra}$ of the inert tracer [a], by a factor which depends on the partitioning of the active species between mud and wall.

Figure 10:
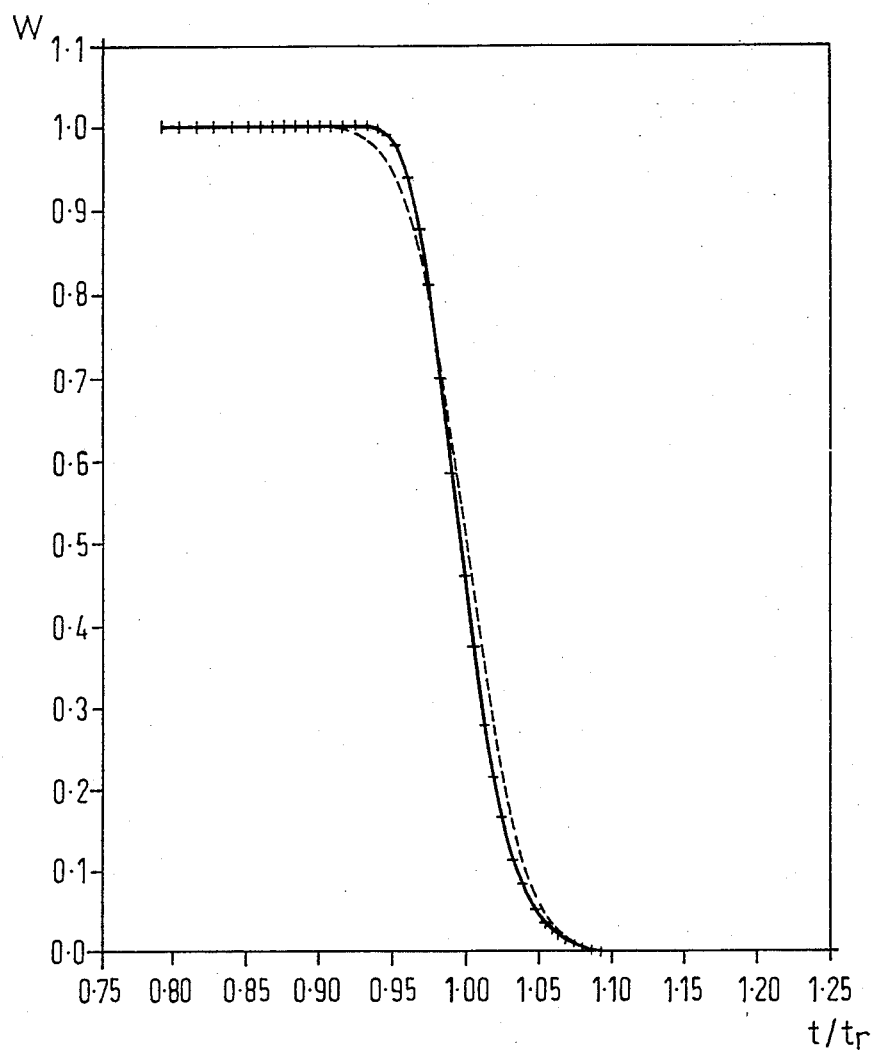
FIG. 10 is a representation of the washout function W (in solid line) plotted against the dimensionless residence time $t/t_r$ and of the tanks-in-series model (dashed line).

During its passage from surface to bottomhole and back to surface, the tracer experiences a series of complicated fluid mechanical circumstances. Any serious attempt to model the internal fluid mechanics of the wellbore system in detail is therefore a major undertaking. For the limited purposes of chemical logging, the present invention proposes to use the time density function, or a function derived from it, to characterize the circulation of fluids in wellbores. The main advantage is to avoid the need for a comprehensive model of the circulation of the fluids; the hydrodynamic dispersion being characterized by a direct measurement of the residence time distribution function f(t) or a function derived from f(t). Ccxparisons between the observed test data and several simple models widely used in the literature can be made. More particularly, it is useful to compute the function F(t)=Integral of f(t)dt frcm t=0 to t=t and a (dimensionless) normalised residence time $t_{nr}$=t/$t_r$. Thus the residence time cumulative distribution function F($t_{nr}$) is obtained easily, together with its complement W($t_{nr}$)=1−F($t_{nr}$), called the washcut function. FIG. 10 shows the washout function W in solid line. A comparison has been made with the answers given from several chemical engineering models. The best fit has been obtained with the so-called "stirred tanks-in-series" (which is widely used in chamical engineering and described, for example, in the already mentioned books "Mixing in Continuous Flow Systems" or "Models for Flow Systems and Chemical Reactors"). This model includes a parameter N, which is the number of tanks of identical volume connected in series. The best fit was obtained for this particular case for N=1017 and is shown in FIG. 10 in dashed line.

I claim:

1. A method for the monitoring of drilling mud circulation in a wellbore, by injecting in a discrete way a known amount or concentration of at least one tracer ion in the supply mud and by analysing on site the return mud for the tracer, said method being characterised in that said tracer ion is substantially non-interactive with the other mud components and with the strata drilled, the concentration of said tracer ion is measured, as a function of time, in the return mud and its residence time density function f(t) is determined from said measured concentration in order to assess the hydrodynamic dispersion of the circulating mud.

2. A method according to claim 1 wherein the mean residence time $t_r$ is determined by calculating the first moment of f(t).

3. A method ccording to claim 1 or 2 wherein the transfer function of the circulating mud is determined by the comparison of the concentrations, as a function of time, of the tracer ion injected in the supply mud and measured in the return mud.

4. A method according to claim 3 wherein the tracer ion is injected in the supply mud as a compact pulse so that its concentration versus time is assimilated to a Dirac delta function.

5. A method according to claim 3 wherein the flowrate Q of the circulating mud is known, characterised in that the volume V of the circulating mud is calculated from the expression $t_r = V/Q$.

6. A method according to claim 1 wherein the loss of tracer ion in the wellbore is determined by comparing the concentration of tracer ion injected in the mud with its concentration in the return mud.

7. A method according to claim 1 wherein the concentration of tracer ion measured in the return mud is corrected for the background of tracer ion present in the mud prior to injection.

8. A method according to claim 1 wherein at least two tracer ions are injected simultaneously in the supply mud and their concentrations, versus time, in the return mud are separately measured.

9. A method according to claim 8 wherein said at least two tracer ions are inert.

10. A method according to claim 8 wherein one of said at least two tracer ions is inert and another one is active with the borehole wall.

11. A method according to claim 1 wherein the washout function W is derived from the residence time density function and is compared with models used in chemical engineering in order to determine which model fits the best with the washout function W.

12. A method according to claim 1 wherein the concentration of tracer ion(s) is determined by ion chromatography.

13. The method as recited in claim 1 including the step of monitoring the chemistry of drilling mud returning from the borehole to produce a chemical log; and correcting the chemical log for the distorting effects of hydrodynamic dispersion.

* * * * *